(12) United States Patent
Milpied (10) Patent No.: US 9,392,950 B2
(45) Date of Patent: Jul. 19, 2016

(54) SYSTEMS AND METHODS FOR DIAGNOSING HEART FAILURE BASED ON SLEEP APNEIC INDICATORS

(71) Applicant: SORIN CRM SAS, Clamart (FR)

(72) Inventor: Paola Milpied, Paris (FR)

(73) Assignee: SORIN CRM SAS, Clamart (FR)

(*) Notice: Subject to any disclaimer, the term of this patent is extended or adjusted under 35 U.S.C. 154(b) by 0 days.

(21) Appl. No.: 14/463,535

(22) Filed: Aug. 19, 2014

(65) Prior Publication Data

US 2015/0057555 A1 Feb. 26, 2015

(30) Foreign Application Priority Data

Aug. 20, 2013 (FR) .................................... 1358092

(51) Int. Cl.
| | |
|---|---|
| A61B 5/0402 | (2006.01) |
| A61B 5/08 | (2006.01) |
| A61B 5/00 | (2006.01) |
| A61N 1/362 | (2006.01) |
| A61N 1/37 | (2006.01) |
| A61N 1/05 | (2006.01) |
| A61B 5/0215 | (2006.01) |
| A61B 5/0452 | (2006.01) |
| A61B 5/11 | (2006.01) |

(52) U.S. Cl.
CPC ............. *A61B 5/0402* (2013.01); *A61B 5/0215* (2013.01); *A61B 5/0452* (2013.01); *A61B 5/0816* (2013.01); *A61B 5/1107* (2013.01); *A61B 5/4806* (2013.01); *A61B 5/4818* (2013.01); *A61B 5/4836* (2013.01); *A61B 5/6869* (2013.01); *A61B 5/746* (2013.01); *A61N 1/0587* (2013.01); *A61N 1/362* (2013.01); *A61N 1/3702* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 2004/0138718 A1* | 7/2004 | Limousin et al. | 607/17 |
| 2005/0085734 A1* | 4/2005 | Tehrani | 600/484 |
| 2007/0167851 A1* | 7/2007 | Vitali et al. | 600/513 |
| 2008/0039730 A1* | 2/2008 | Pu et al. | 600/484 |
| 2012/0259379 A1* | 10/2012 | Casset et al. | 607/18 |

FOREIGN PATENT DOCUMENTS

| | | |
|---|---|---|
| EP | 0 515 319 A1 | 11/1992 |
| EP | 0 719 568 | 7/1996 |
| EP | 0 750 920 | 1/1997 |

(Continued)

OTHER PUBLICATIONS

Preliminary Search Report for French Patent Application No. FR1358092, dated Jan. 15, 2014, 2 pages.

*Primary Examiner* — Erica Lee
(74) *Attorney, Agent, or Firm* — Foley & Lardner LLP (57) ABSTRACT

This device includes a sensor of endocardiac acceleration EA and one or more circuits configured for: extracting from the EA signal a predetermined EA parameter, determining a period of sleep, evaluating the clinical condition of the patient based on the EA parameter variations on this sleep period, and issuing an alert of worsening of the patient's condition. The device further determines a variability index of the EA parameter on the sleep period, and then calculates a ratio between this calculated variability index and a reference value, and delivers this ratio as a clinical status index. The alert signal is generated by the crossing by this ratio of a predetermined alert threshold.

20 Claims, 5 Drawing Sheets

(56) References Cited

FOREIGN PATENT DOCUMENTS

| EP | 0 770 407 | 5/1997 |
| EP | 1 317 943 | 6/2003 |
| EP | 1 413 330 | 4/2004 |
| EP | 1 433 496 | 6/2004 |
| EP | 1 741 386 | 1/2007 |
| EP | 1 741 387 | 1/2007 |
| EP | 1 867 360 A2 | 12/2007 |
| EP | 2 092 885 A1 | 8/2009 |

* cited by examiner

SYSTEMS AND METHODS FOR DIAGNOSING HEART FAILURE BASED ON SLEEP APNEIC INDICATORS

CROSS-REFERENCE TO RELATED APPLICATION

This application claims the benefit of and priority to French Patent Application No. 1358092, filed Aug. 20, 2013. French Patent Application No. 1358092 is hereby incorporated by reference in its entirety.

BACKGROUND

The invention relates to "active implantable medical devices" as defined by Directive 90/385/EEC of 20 Jun. 1990 the Council of the European Communities. The invention may relate to devices for cardiac pacing, resynchronization and/or defibrillation for diagnostics and treatment of cardiac arrhythmias, including active implants for purely diagnostic purposes. It relates in particular to preventive diagnosis of the risk of cardiac decompensation by methods of analysis algorithms of the signals collected by an implantable device. The diagnosis can be particularly useful with the implants implementing resynchronization functions.

Resynchronization is a technique called "CRT" (Cardiac Resynchronization Therapy) or "BVP" (Bi-Ventricular Pacing). This technique typically includes delivering a joint and continuous stimulation to the left and right ventricles, with potential application of a delay between the respective moments of stimulation. The delay is called interventricular delay or VVD. This delay is adjusted to resynchronize the contraction of both ventricles, which improves the hemodynamic status of the patient by optimizing the contraction/relaxation cycle with a direct benefit to the heart.

Long-term effects of the CRT therapy on heart failure patients, however, may be very different. These effects may be assessed by determining the left ejection fraction and the NYHA class of heart failure and the comparison of initial data with, for example, reassessed data after six months of treatment with CRT therapy.

An improved clinical status is found in the majority of patients (reflected by an increase in the left ejection fraction), while for some other patients, no significant improvement is seen. And yet, for some other patients there is, on the contrary, a worsening of the clinical condition, with decreased left ventricular ejection fraction, even with an increase in NYHA class.

Some of the patients that are non-responders to CRT therapy suffer from sleep apnea, more precisely central (non obstructive) apneas. Central apnea, which has a neurological cause and does not result from an obstacle to inspiration, may indeed appear as a result of heart failure. Therefore, the implementation of alerts concerning the risks of decompensation in heart failure patients with sleep apnea would allow changing and adapting without delaying treatment, and prevent hospitalizations.

EP 1433496 A1 (ELA Medical) discloses a device equipped with methods for measuring a parameter called HRV (Heart Rate Variability) to characterize the occurrence of episodes of apnea or hypopnea. The analysis is of the RR segment variability, thus purely in the temporal domain. This document also does not address in any way the question of heart failure patients.

EP 1413330 A1 (ELA Medical) proposes to monitor the signal of minute ventilation (MV signal) to detect the episodes of apnea or hypopnea and simultaneously assess the myocardial contractility, e.g. by analysis a transthoracic impedance signal or an endocardial acceleration signal. In case of significant variation in contractility during an apnea or hypopnea episode, the device temporarily modifies a pacing parameter, e.g. the frequency of stimulation or the atrioventricular delay in the case of a dual chamber device. This action can compensate the oxygen desaturation resulting from the failure of the sympathetic system activity during episodes of respiratory disorder, by increasing the flow. The purpose of this known device is to trigger a particular reaction of the device during the episodes of apnea only if this reaction is appropriate. The method does not include not a long-term monitoring of the clinical status of a heart failure patient, or the triggering of alerts in case of worsening of this clinical status proved in the long term.

EP 1741386 A1 (ELA Medical) describes a device wherein the occurrence of episodes of apnea is not detected by analysis of a MV or transthoracic impedance signal, but by that of an endocardial acceleration (EA) signal. A sudden depression of cardiac contractility, associated with the occurrence of an apnea or hypopnea, activates an alert that can be used to initiate appropriate therapy (increase in pacing rate) and/or document diagnosis episode information in a memory of the device: marker of occurrence of apnea, duration of the alert, or other information.

EP 1741387 A1 (ELA Medical) describes a device of the same type, operating from an external device including a cardiophonographic sensor pressed against the chest wall and an EEG machine, therefore applicable to patients not implanted with a cardiac pacemaker. In any event, this document does not address the specific problem of the diagnosis of heart failure.

EP 1867360 A2 (ELA Medical) proposes to combine between them various signals from an activity sensor (G sensor, accelerometer), a physiological sensor (MV sensor, minute ventilation) and an endocardial acceleration sensor (EA sensor). Algorithms of the respective analysis each produce a warning signal of cardiac decompensation and cross-analysis methods provide a composite signal of preventive alert, on different levels, depending on a number of specific indexes that may reveal a worsening of the clinical condition of the patient.

However, this approach does not aim to evaluate the effectiveness of CRT therapy, and shows no particular sensitivity or specificity for patients who are non-responders to CRT therapy, which is the main problem to be solved by embodiments of the present invention. Indeed, besides the fact that this known technique does not attempt to detect the possible occurrence of episodes of sleep apnea, the overall evaluated clinical condition is sensitive to factors such as the general activity level of the patient, the goal being to detect and take into account any reductions in activity when the patient spares himself after he has experienced first crisis occurring during exercise. But these factors are not significant when the deterioration in cardiac status is correlated with disturbances of sleep apnea; they may even prevent early detection of risk of cardiac decompensation, in particular in cases wherein the patient maintains a stable level of activity as long as he is not faced with a sudden worsening of his condition.

SUMMARY

Embodiments of the present invention may overcome the above presented difficulties and limitations. Embodiments of the present invention may include a mechanism to assess, with high sensitivity and selectivity, the effect due to a respiratory disease such as central sleep apnea, specifically on the evolution of the clinical status of heart failure patients.

Embodiments of the present invention also provide a device which is particularly and specifically adapted to the rapid discrimination of non-responder patients in a population of patients implanted with a CRT device, so as to promptly diagnose these patients and avoid to perpetuate ineffective or harmful therapy. The device may also quickly reassess the applied therapy in order to avoid a deterioration of the general condition of the patient and possible hospitalization thereof.

Embodiments of the invention also provide such a device that requires no direct measurement of a signal of periodic breathing, that is to say which does not need to specifically detect the occurrence of each episode of apnea or hypopnea. Indeed the present invention assesses the impact of this respiratory disorder on the clinical condition of heart failure patients; it is not to take an immediate compensating action (increased heart rate, etc.) in response to apnea when it occurs.

Embodiments of the present invention include a sensor adapted to output an endocardial acceleration EA signal; signal analysis methods, capable of extracting from the EA signal a predetermined EA parameter and of storing this EA parameter on the successive cardiac cycles; methods for determining a period of sleep of the patient; and methods for evaluating the patient's hemodynamic status, adapted to provide an indication of the clinical status of the patient implanted with the device, according to the variations of said EA parameter on said sleep period of the patient.

According to embodiments of the invention, the evaluation methods calculate a variability index of the EA parameter on the sleep period, calculate a ratio between the calculated variability index and a reference variability index value, and output the ratio as clinical condition index. The value of reference variability index can be a predetermined fixed value or, preferably, a value of the variability index initially calculated and then stored by the evaluation methods. The device further includes methods for diagnosis of heart failure, capable of delivering an alert signal of worsening of the patient condition in response to the crossing by said ratio of a predetermined alert threshold. The variability index is determined from the standard deviation of the EA parameter values over the period of sleep, preferably the standard deviation weighted by the average of these values over the same period.

Finally, the device may include methods for, when the ratio exceeds a predetermined threshold of improvement of the patient status lower than the predetermined alert threshold, updating, by the calculated current variability index, the value of the reference variability index stored by the evaluation methods.

The EA parameter can be a parameter of the group consisting of: the peak-to-peak value of the EA1 component; the peak-to-peak value of the EA2 component; the time interval between the start of the EA1 component and the start of the EA2 component; the time of onset of the EA1 component, represented by the interval between i) a temporal marker of start of the cardiac cycle and ii) the crossing of a magnitude or energy threshold of the EA1 component; the time interval between i) the crossing of the amplitude or energy threshold of the EA1 component and ii) the moment of the EA1 component peak; and a composite parameter combining previous settings. The EA1 component is the component corresponding to the first peak of the EA signal associated with the isovolumetric ventricular contraction, and the EA2 component is the component corresponding to the second peak of the signal associated with the EA isovolumetric ventricular relaxation.

According to various advantageous embodiments:

The device may include an internal clock and methods adapted to restrict determination of the sleep period to a predetermined daily time slot.

The device may include methods of detection of activity phases of the patient, and methods for excluding from the calculation of the variability index parameter the values of the EA parameter stored during the detected activity phases during the period of sleep.

The device may include methods for detecting phases of patient wake and methods for excluding from the calculation of the variability index the values of the EA parameter stored during phases of wake detected during the sleep period.

The device may include a counter of crossings by the ratio of the predetermined threshold alert, and the diagnostic methods shall issue the alert signal only when the counter reaches a predetermined cumulative value; preferably, the counter is incremented only in case of consecutive crossings of the predetermined threshold.

BRIEF DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

The present invention can be applied to implantable devices such as that of the Paradym family (in particular the Paradym RF SonR CRT-D) and produced and marketed by Sorin CRM, Clamart, France. Embodiments described herein include programmable microprocessor circuitry to receive, format and process electrical signals collected by implantable electrodes. Some embodiments include circuitry for delivering stimulation pulses to these electrodes. The method of the invention is implemented primarily by software (i.e., computer code stored in a memory device) and by appropriate algorithms executed by a microcontroller or a digital signal processor.

Various embodiments disclosed herein are based on the analysis of the endocardial acceleration (hereinafter "EA"), which is a parameter that reflects very precisely and in real time the phenomena that contributes to the mechanical functioning of the myocardium and can be measured by an accelerometer coupled to the heart muscle, as described for example in EP 0515319 A1 (Sorin Biomedica Cardio SpA). This EP document describes a method to obtain an EA signal through an endocardial lead with a stimulation distal electrode implanted in the atrium or in the ventricle and incorporating a microaccelerometer for measuring the endocardial acceleration.

Such a sensor may for example be arranged on an endocardial lead terminating at the bottom of the ventricle and provided at this place of an acceleration sensor. It may also be an atrial lead provided at its one end disposed against the wall of the right atrium of an acceleration sensor. Note, however, that although in the present description it is mainly referred to an EA signal delivered by a sensor located on an endocardial lead, the invention is also applicable to an analysis made from an EA signal issued by other types of implantable sensors, such as a motion sensor of a myocardial wall, an epicardial sensor or an accelerometer placed in the case of an implant. The invention is also applicable to the analysis of an external EA signal obtained noninvasively, for example from a sensor attached to the patient's chest at the sternum.

Figure 1:
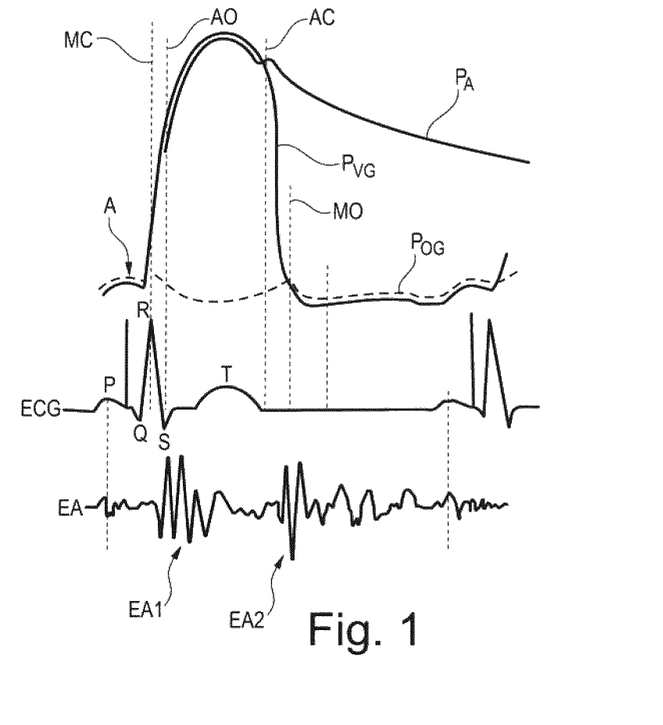
FIG. 1 is a series of graphs illustrating three different characteristic signals collected during a cardiac cycle.

FIG. 1 illustrates the various signals characterizing the activity of the heart during a cardiac cycle, with:

The profile of intracardiac pressures $P_A$, $P_{VG}$ and $P_{OG}$: the characteristic $P_A$ shows the variations in the aortic pressure, $P_{VG}$ those of the left ventricular and $P_{OG}$ those of the left atrium. These variations go through the following phases: a contraction of the left atrium, closure of the mitral valve (MC), opening of the aortic valve (AO), closure of the aortic valve (AC), and opening of the mitral valve (MO);

A surface electrocardiogram record (ECG) with successively: the P wave corresponding to the depolarization of the atria, the QRS complex corresponding to the depolarization of the ventricles, and the T wave of ventricular repolarization; and The variations in the collected endocardial acceleration EA signal, forming two main components, EA1 and EA2, during a given cardiac cycle, corresponding to the two major heart sounds (S1 and S2 sounds of phonocardiogram) possible to recognize in each cardiac cycle.

Figure 2:
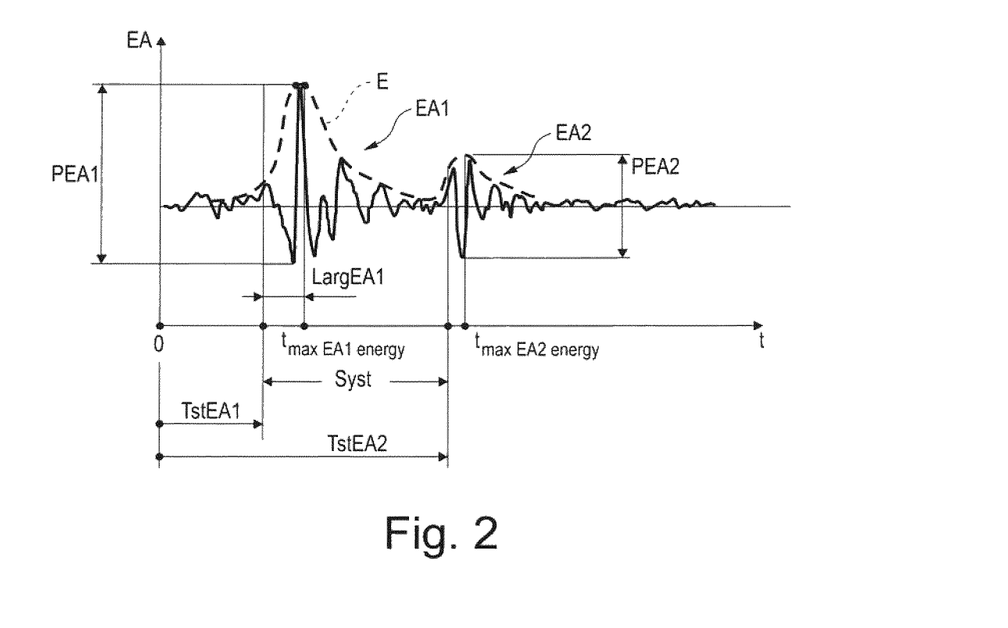
FIG. 2 shows in more detail the shape of the endocardiac acceleration signal within a given cycle.

In FIG. 2, the variations of this EA signal during a cardiac cycle are more precisely is illustrated. The EA1 component is shown, which begins after the QRS complex and is caused by a combination of the closing of the atrioventricular valves (mitral and tricuspid valves), the opening of the semilunar valves (aortic and pulmonary valves) and the contraction of the left ventricle. The amplitude variations of this EA1 component are closely related to the changes in the pressure in the ventricle, the maximum peak-to-peak PEA1 being specifically correlated to the positive maximum of the pressure variation dP/dt in the left ventricle. Also shown is the EA2 component, which occurs during the isovolumetric ventricular relaxation phase. It accompanies the end of the ventricular systole and is mainly produced by the closure of aortic and pulmonary valves.

For the implementation of the invention, a predetermined parameter, hereinafter called "EA parameter", must be extracted from the EA signal, which will be used to characterize the presence or absence of central sleep apnea. This EA parameter is obtained by a method such as that described in EP 2092885 A1 (ELA Medical), which is useful for eliminating the cycle to cycle variations by temporally readjusting the successive components before averaging them.

Essentially, the EA signal is subject to a preliminary processing including individualizing the successive cardiac cycles in the EA signal continuously collected, in identifying markers of the start of the cycle to separate and to isolate in these cycles a series of temporally bounded EA sub-signals each corresponding to the duration of one cardiac cycle. In the case of an endocardial EA signal, the temporal markers of a cycle start can be provided by the implant itself or by an external device during implantation, which according to the operating mode, stores in memory the moments of the V stimulation, or the moments of detection of the R-wave.

The next step is to isolate the EA1 and the EA2 components in each of the temporally bounded sub-signals corresponding to one cardiac cycle. Each of these EA1 and EA2 components is represented by a set of successive values describing the continuous variation of the EA signal in a given temporal window extending around the peak reached by the EA signal (PEA1 peak or PEA2 peak), on a fraction of the duration of a cardiac cycle. Specifically, each component will be constituted of a subset of the samples obtained after the EA signal has been scanned on the duration of the cardiac cycle.

Each of these components thus represents a fraction of the EA signal on the duration of a cardiac cycle, each cardiac cycle including a plurality of different components that follow each other. Preferably, the EA1 and EA2 components of the EA signal are determined with an averaging over several cycles, typically three to five cycles, using a technique such as that disclosed in the aforementioned EP 2092885 A1, a technique that allows in particular to eliminate the cycle to cycle variations by temporally readjusting the successive components before averaging them. This technique may include performing a pre-processing of the continuously collected EA signal, with cutting of the EA signal into sub-signals each corresponding to the duration of a cardiac cycle and identified by a marker of cycle start enabling this cutting and then segmenting of each of these sub-signals so as to individualize the EA1 and EA2 components in a given temporal window. Then, for the current EA1 or EA2 component thus isolated on a cycle, looking for a correlation peak with respect to the EA1 (or EA2) components of the other collected cycles, computing of a corresponding temporal shift, and applying the calculated temporal shift to the current component, so as to align it with respect to the other. Analytical processing can then be performed on these successive EA1 and EA2 components, with elimination of the bias of the cycle to cycle variability through this pre-processing.

The predetermined EA parameter, which will be used to characterize the presence or absence of central sleep apnea, is preferably the PEA1 amplitude of the first peak of endocardiac acceleration, that is to say the maximum peak-to-peak value separating the two extrema, positive and negative, of the EA1 component of the acceleration signal. This PEA1 parameter will be used in the following description as the characteristic parameter, but this choice is, however, not limitative.

In general, it is possible to use as the EA characteristic parameter (see FIG. 2):

The peak-to-peak of the EA1 component, designated PEA1;

In a comparable way, the peak-to-peak of the EA2 component designated PEA2;

The timing of the start of the EA1 component, noted TstEA1, which is a duration counted from the time origin O in FIG. 2 (instant of the V stimulation or of the R-wave detection, corresponding to a marker of the beginning of the cycle);

An indicator of the length of the EA1 component, designated LargEA1, which is the time interval between TstEA1 and the instant $t_{max}$EA1 energy of occurrence of the energy peak of the EA1 component;

The time interval Syst separating TstEA1, which marks the beginning of the EA1 component, and TstEA2, which marks the beginning of the EA2 component, this interval corresponding to the duration of the systole (the timings TstEA1 and TstEA2 of the start of the EA1 and EA2 components can be obtained for example by thresholding an energy envelope E obtained by squaring the value of the signal samples and then applying a smoothing window, and thresholding); and/or A composite parameter combining with appropriate weighting a plurality of the previous settings.

It has been observed that at least 50% of heart failure patients have sleep apnea. In some cases, the condition is an obstructive apnea, largely associated with obesity, which is the most common apnea and is produced by an obstruction of the upper airway (nose, mouth, larynx, and pharynx). The other type of sleep apnea, namely the so-called central apnea, has a neurological cause, so without a cause related to the respiratory system. Unlike obstructive apnea, central apnea can occur as a result of heart failure, so that a proved increase of central apneas in a patient with heart failure indicates a need to intensify therapy related to heart failure.

In clinical studies, the instability of the EA signal is a decompensation marker in heart failure patient. In other words, the more the patient deteriorates, the more increase of the EA variability signal. The implementation of alerts related to the risk of decompensation in patients with heart failure due to an increase in sleep apneas would change treatments and therapies, and prevent hospitalizations.

Assessing this variability only during sleep stages, in order to have an index of clinical activity not related to the patient condition (and that on the contrary is mainly influenced by the number of sleep apneas) can lead to much better values of sensitivity and specificity in respect of that particular condition.

The variability of the EA signal—which is the key parameter of the technique of the invention—is to be distinguished from the variability of heart rate or HRV (Heart Rate Variability) which is a different parameter, sometimes used to assess the long-term evolution of the heart failure patient. Specifically, HRV reflects the ability of the heart to adapt to changing circumstances, so that stability or low variability in the heart rate is a sign of deterioration of the patient's condition. In contrast, in the case of the invention, the analysis is performed during a sleep period, a period without effort or disturbance, wherein the heart rate is naturally and normally stable so that the contractility should not have to adapt. Thus, if there is an increase in the variability of the EA signal during periods of sleep, this shows a chaotic behavior of the heart, revealing a worsening of the clinical status of the heart failure patient.

Figure 3:
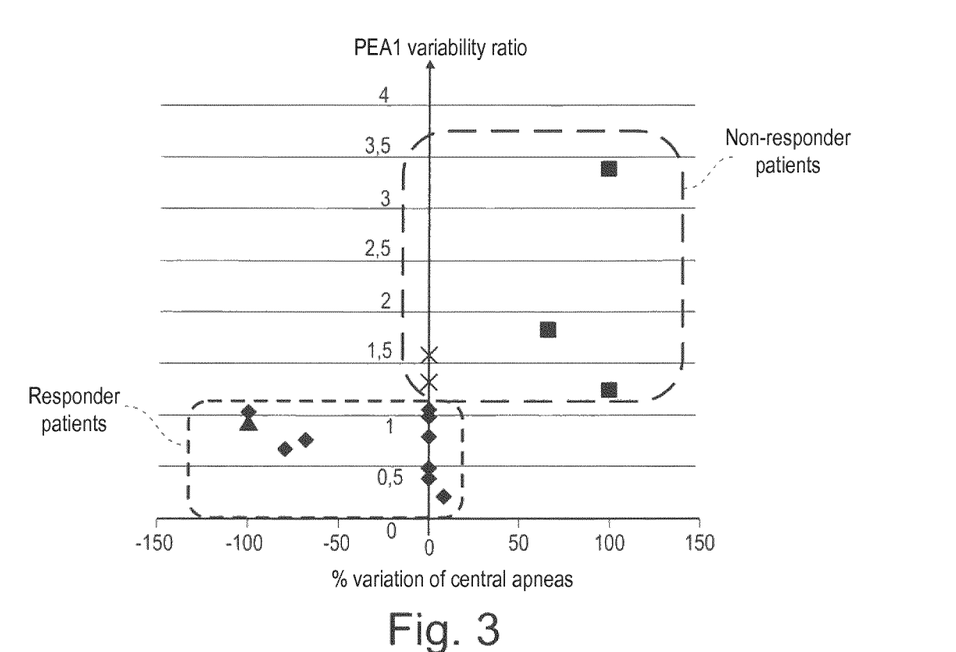
FIG. 3 is a diagram showing the distribution of patients undergoing CRT therapy, between responders and non-responders, as a function of the central apnea rate and of the variability ratio of the amplitude of the first peak of endocardial acceleration.

FIG. 3 shows the results of a clinical study on fifteen patients implanted with a CRT device. These patients were subjected to a first polysomnographic analysis before implantation of the device and then a second analysis six months after. During each of these examinations, an EA signal was recorded in order to determine the variability (standard deviation divided by the mean value) of the PEA1 during sleep and in the most common position, to overcome the EA signal changes associated with the position of the patient (insofar as in this study, the patients were equipped with an external sensor; in the case of an endocardial sensor this factor would have no influence). The ratio of the variability between the two PEA1 examinations was calculated and plotted on the ordinate in FIG. 3, with in abscissa the rate of change of central apneas.

A first group of patients, responders to the CRT therapy, is observed. These patients show an improvement of at least one NYHA class (diamonds in FIG. 3), or a significant increase in the left ejection fraction in the same NYHA class (triangle in FIG. 3). Another group of patients, however, do not respond to the CRT therapy, and exhibit a worsening of at least one NYHA class (squares in FIG. 3) or show no significant increase in the left ejection fraction in the same NYHA class (crosses in FIG. 3). It can be seen that for the responder patients, the ratio of PEA1 variability does not exceed 1.1, while for non-responder patients, this ratio is greater than 1.2.

Figure 4A:
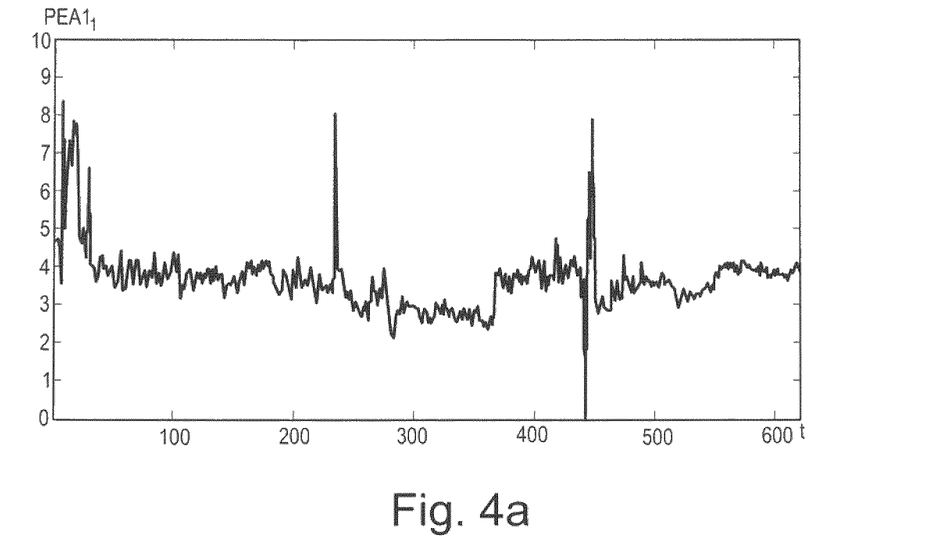
FIGS. 4a and 4b are records of changes in the amplitude of the first peak of endocardial acceleration over time during a sleep period of a non-responder patient, respectively at the beginning of therapy and after six months, showing the marked increase in the variability of this amplitude value over the deterioration of the general condition of the patient.
Figure 4B:
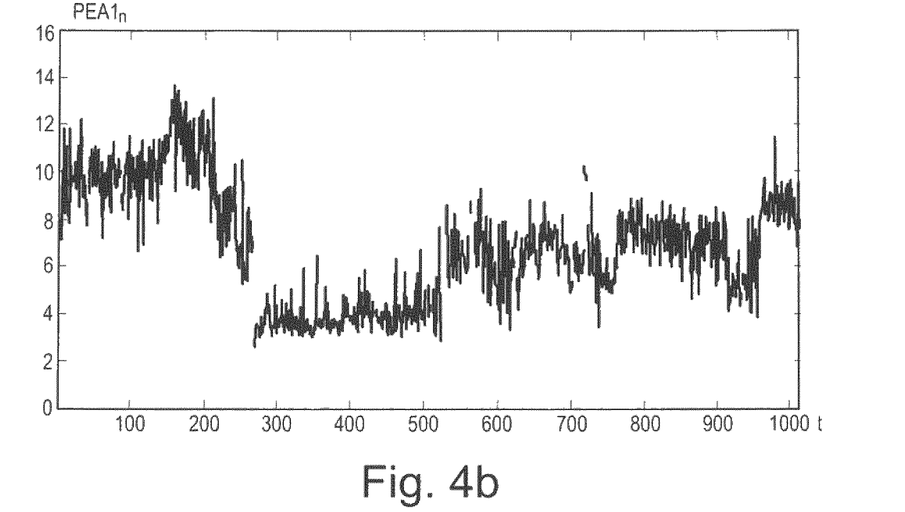

FIGS. 4a and 4b are records of changes in the amplitude of the first peak of endocardial acceleration over time during a sleep period of a non-responder patient, respectively at the beginning of therapy (FIG. 4a) and six months after (FIG. 4b), showing marked increase in the variability of this amplitude value as the general status of the patient degrades. In this patient, after six months of application of the CRT therapy, the NYHA class III has deteriorated to IV, the left ejection fraction decreased from 23 to 12, and the average number of central apneas per hour increased from 22 to 45. The ratio of PEA variability between the two examinations is 1.23.

It is contemplated by the present invention to provide an alert when the patient is not responding to the CRT therapy, based on the value of the ratio that may reflect the increase or decrease in the number of central apneas. With a threshold of 1.2, in the case of the fifteen patients described above, the specificity and sensitivity would thus be of 100%.

Figure 5:
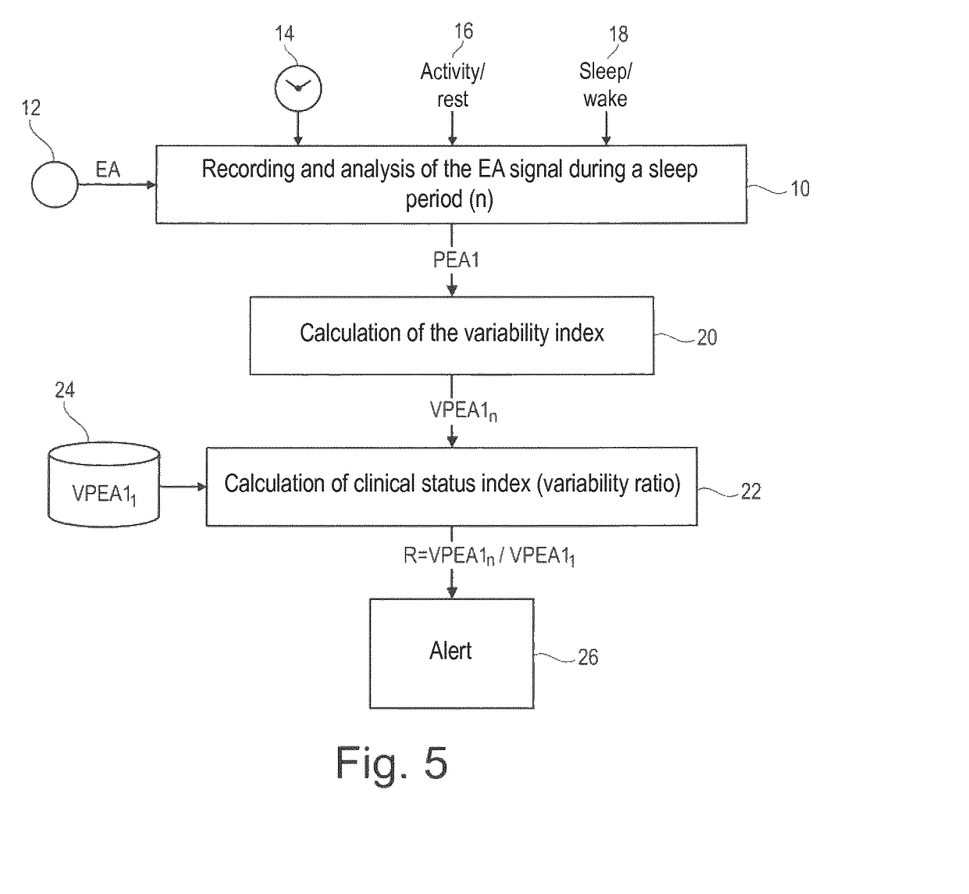
FIG. 5 schematically illustrates the various parameters for the evaluation according to the invention of the clinical condition of the patient, and the successive phases of calculating of an index representative of this clinical condition.

The method by which this characteristic ratio is evaluated and the alert is triggered if necessary will now be described in more detail, with reference to FIGS. 5-7. FIG. 5 schematically illustrates the various parameters involved to that purpose, as well as the successive phases of calculation of an index representative of the patient's clinical condition. Block 10 schematically shows the recording capabilities of the EA signal analysis for a period of sleep of index n. The EA signal is issued by a sensor 12, internal or external, preferably an integrated sensor within an endocardial lead connected to the generator of a CRT device. An internal clock 14 is used to define the predetermined temporal windows, while a suitable sensor, for example an acceleration sensor (G sensor) outputs a signal 16 indicative of a state of activity or of rest of the patient.

Discrimination 18 between the phases of sleep and phases of wakefulness can be made by various means. The simplest technique is to use the internal clock of the device 14, switching an indicator at fixed times. It is also possible, as taught by EP-A-0719568A1 (ELA Medical) to make a discrimination between the waking and sleeping by signal analysis of minute ventilation (MV). Indeed, the circadian variations of the frequency and of the amplitude of the successive respiratory cycles of the patient is well reproduced by this signal, and a calculation of the average ventilation over 24 hours allows to make a discrimination between a waking ventilation and a sleep ventilation. One can use in addition the activity sensor 18, the signal of which can detect patient movement. Information of this type of the sensor is in itself not very specific of the phases of sleep and wakefulness, but it is known to combine the signals from a G sensor and a MV sensor to derive meaningful information, as described for example in EP-A-0750920A1, EP-A-0770407A1 and EP1317943A1 (ELA Medical), which can be referred to for further details.

Block 10 estimates on successive cycles of this sleep period the value of the selected representative EA parameter, which in this example is the amplitude PEA1 of the first peak of the EA1 component of the EA signal. The PEA1 value is measured at each detected cardiac cycle, preferably with exclusion of the components collected during possible phases wherein a wake and/or an activity are detected during the considered sleep period (all night). An average value is calculated on a sliding window, for example, 60 seconds, with 30 seconds of recovery between the successive windows, the sleep/wake status being given every 30 seconds. From these successive measurements, the device evaluates (block 20) a variability index $VPEA1_n$ along the night of rank n, this index being calculated as the standard deviation of successive PEA1 values over the period n, divided by the average of these PEA1 values over the length of the night.

Note that this definition of variability is not exhaustive and that other indices of variability can be considered, for example simply from the standard deviation of PEA1 values not weighted by the average of these values over the same period, or the standard deviation, weighted or not, of other EA parameters such as those described with reference to FIG. 2.

As noted above, in the present invention rather than the absolute value of the variability $VPEA1_n$, it is preferred to focus on the evolution of this variability, in order to highlight a change of status without judging the clinical status at any given time. For this, a ratio between two variabilities is estimated (block 22), namely the current variability $VPEA1_n$ and the initial variability $VPEA1_1$, stored in a memory 24 of the device. This ratio $R=VPEA1_n/VPEA1$ is compared to a predetermined threshold. If the variability has increased over last night, we can conclude a worsening of the clinical condition of the patient in terms of the number of central apneas and thus of heart failure, leading to triggering an alert indicating a risk of cardiac decompensation (block 26).

Figure 6:
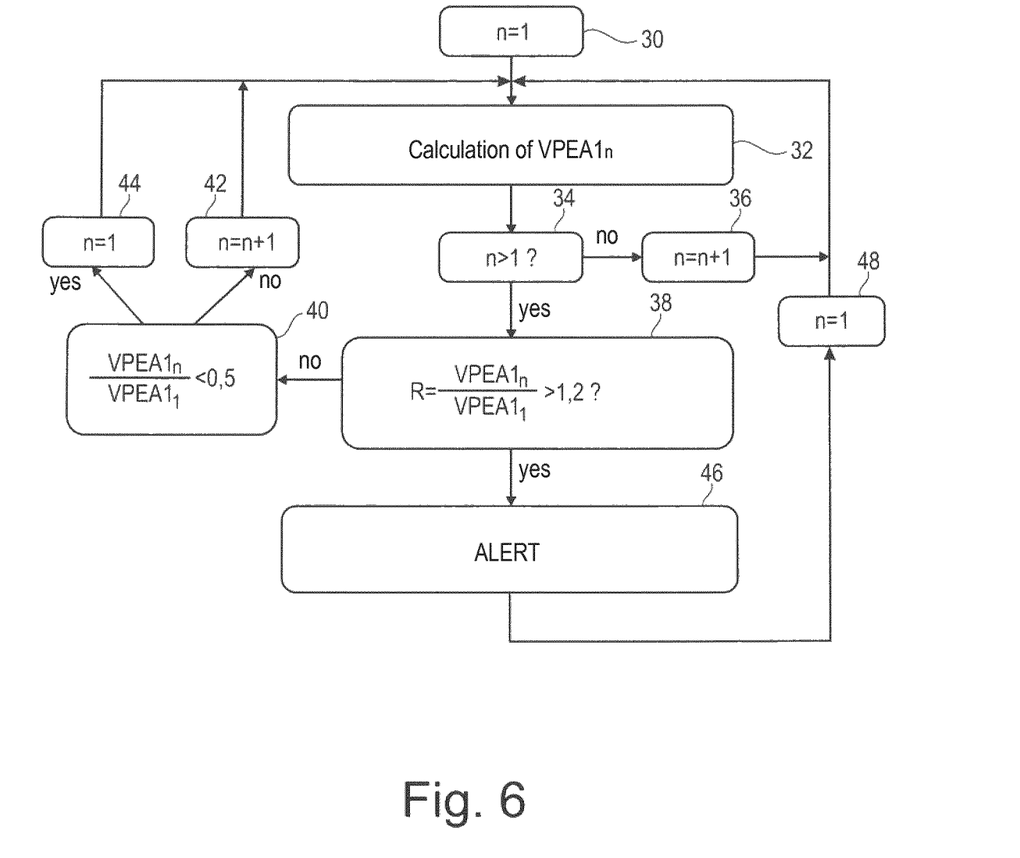
FIG. 6 is a simplified flow chart explaining the different steps to be implemented to assess the patient's clinical status and to trigger an alert if necessary, according to a first embodiment of the invention.

FIG. 6 more precisely illustrates the algorithm for calculating the ratio of the variability and of possible triggering of the alert. The index n, set to n=1 (block 30) indicates the successive ranks of the night during which the patient is evaluated. After calculating the variability $VPEA1_n$ (block 32), in the case of the first night (test 34) the value of $VPEA1_1$ is stored and the index n is incremented by one (block 36) before calculation of the next value of variability $VPEA1_n$.

If the test 34 indicates that the night is not the first one, then the ratio $R=VPEA1_n/VPEA1_1$ is calculated and compared to the predetermined threshold, which is for example 1.2 (block 38). If this threshold is not exceeded, the ratio is compared to another threshold, substantially lower, e.g. a 0.5 threshold (block 40). If R is less than this other threshold, this means that the variability is significantly lower during the last night and we can therefore conclude to a significant improvement in the patient's condition. The reference value $VPEA1_1$ should then be updated by putting the index n at 1 (block 44). Otherwise, the index n is incremented by one (block 42) before calculation of the variability $VPEA1_n$ for the next night (block 32).

If, during the test 38, the ratio R exceeds the predetermined alert threshold, then it can be concluded that a worsening of the patient's condition is occurring, which leads to triggering the alert (block 46).

If during successive nights the ratio never exceeds the fixed limit value (1.2 in this example), it does not necessarily mean that the patient is responding to the CRT therapy, but only that the number of apneas was not significantly increased and that it does not allow concluding there is aggravation. Other parameters can then be measured and evaluated to detect a worsening of the heart failure which would not be correlated with an increase in central apneas, as described for example in EP1867360A2 above.

Figure 7:
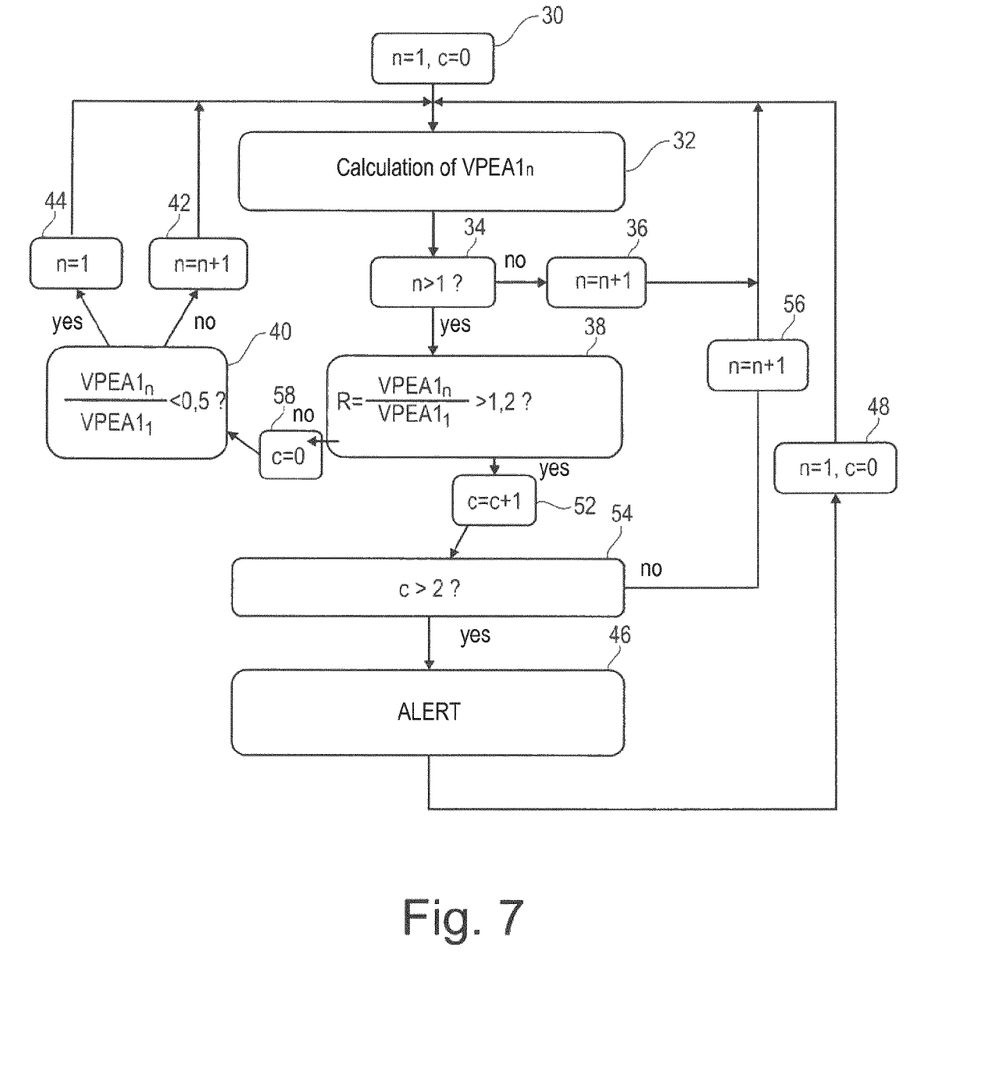
FIG. 7 is similar to FIG. 6 for a second embodiment of the invention.

FIG. 7 shows a variant of FIG. 6, which provides not to systematically trigger the alert 46 when the threshold of the test 38 is exceeded, but only in case of successive crossings, for example when this threshold is exceeded during two consecutive nights. For this purpose, the algorithm (whose blocks corresponding to the same functions are referenced identically to that of in FIG. 6) includes an additional counter c of crossings, initialized to zero at block 30. In case of exceeding the threshold at test 38, this counter is incremented (block 52), and its value is then tested in block 54. If c is 1, only the index n is incremented (block 56) and the method is repeated. Otherwise, this means that the threshold has been crossed during the previous night and it is then necessary to activate the alert (block 46). If the threshold has been crossed once but not repeated in the next night, then the counter c is reset (block 58) to avoid a false alert, or in situations wherein the ratio is close to the triggering threshold, requiring confirmation of the alert the next night.

The invention claimed is:

1. An active medical device, such as a stimulation, resynchronization and/or defibrillation implantable device, or a device for diagnostic purposes, including:
    a sensor adapted to receive an endocardial acceleration (EA) signal;
    one or more circuits configured for:
        performing signal analysis by extracting from the EA signal a predetermined EA parameter, and storing this EA parameter for successive cardiac cycles;
        determining a first sleep period of the patient;
        evaluating the patient's hemodynamic status by providing an indication of the clinical status of the patient with the device according to the variations of said EA parameter on said first sleep period of the patient, wherein evaluating the patient's hemodynamic status comprises:
            calculating a variability index of said EA parameter on the first sleep period, calculating a ratio between said calculated variability index and a value of a reference variability index of said EA parameter, wherein the value of the reference variability index is a calculated variability index of a second sleep period of the patient, wherein the second sleep period occurs prior to the first sleep period, and
        delivering said ratio as clinical condition index; and
        diagnosing heart failure and delivering an alert signal of worsening of the patient condition in response to the crossing by said ratio of a predetermined alert threshold.

2. The device of claim 1, wherein said variability index is determined from the standard deviation of the values of the EA parameter on the first sleep period.

3. The device of claim 2, wherein said variability index is the standard deviation of the values of the EA parameter on the first sleep period, weighted by the average of these values over the same first sleep period.

4. The device of claim 1, wherein said EA parameter is one parameter of the group consisting of:
    the value of the peak-to-peak of a first EA component (EA1);
    the value of the peak-to-peak of a second EA component (EA2);
    the time interval between the start of the EA1 component and the start of the EA2 component;

the time of onset of the EA1 component, represented by the interval between i) a temporal marker of the start of the cardiac cycle and ii) the crossing of an amplitude or energy threshold of the EA1 component;

the time interval between i) said crossing of the amplitude or energy threshold of the EA1 component from ii) the instant of the peak of the EA1 component; and a composite parameter combining the above parameters, the EA1 component being the component corresponding to the first peak of the EA signal associated with the ventricular isovolumetric contraction and the EA2 component being the component corresponding to the second peak the EA signal associated with the isovolumetric ventricular relaxation.

5. The device of claim 1, further comprising an internal clock adapted to cause restriction of the determination of the first sleep period to a predetermined daily schedule.

6. The device of claim 1, further comprising an activity sensor for the detection of activity phases of the patient, and wherein the one or more circuits are further configured to exclude from the calculation of the variability index the values of the EA parameter stored during activity phases detected during the first sleep period.

7. The device of claim 1, further comprising a wake sensor for detection of wake phases of the patient, and wherein the one or more circuits are further configured to exclude from the calculation of the variability index the values of the EA parameter stored during wake phases detected during the first sleep period.

8. The device of claim 1, further comprising a counter of crossing by said ratio of said predetermined alert threshold, and wherein the alert signal is issued when the counter reaches a predetermined cumulative value.

9. The device of claim 8, wherein the counter is incremented only in case of consecutive crossings of said predetermined threshold.

10. The device of claim 1, wherein said second sleep period is an immediately preceding sleep period.

11. The device of claim 1, wherein said second sleep period is a preceding sleep period other than an immediately preceding sleep period.

12. The device of claim 11, wherein the one or more circuits are further configured to update said value of reference variability index by the value of the calculated current variability index when said ratio exceeds a predetermined threshold of patient status improvement lower to said predetermined alert threshold.

13. A method for diagnosing heart failure using an implantable medical device, comprising the steps of:
receiving an endocardial acceleration signal from a sensor coupled to the implantable medical device;
performing signal analysis by extracting from the EA signal a predetermined EA parameter, and storing this EA parameter for successive cardiac cycles;
determining a first sleep period of the patient;
evaluating the patient's hemodynamic status by providing an indication of the clinical status of the patient with the device according to the variations of said EA parameter on said first sleep period of the patient, wherein evaluating the patient's hemodynamic status comprises:
calculating a variability index of said EA parameter on the first sleep period, calculating a ratio between said calculated variability index and a value of a reference variability index of said EA parameter, wherein the value of the reference variability index is a calculated variability index of a second sleep period of the patient, wherein the second sleep period occurs prior to the first sleep period, and delivering said ratio as clinical condition index; and
diagnosing heart failure and delivering an alert signal of worsening of the patient condition in response to the crossing by said ratio of a predetermined alert threshold.

14. The method of claim 13, further comprising determining said variability index by calculating the standard deviation of the values of the EA parameter on the first sleep period.

15. The method of claim 13, further comprising detecting activity phases of the patient and excluding from the calculation of the variability index the values of the EA parameter stored during activity phases detected during the first sleep period.

16. The method of claim 13, further comprising detecting wake phases of the patient and excluding from the calculation of the variability index the values of the EA parameter stored during wake phases detected during the first sleep period.

17. The method of claim 13, further comprising counting, by a counter, of crossing by said ratio of said predetermined alert threshold, and issuing the signal when the counter reaches a predetermined cumulative value.

18. A method for diagnosing heart failure in a patient using an implantable medical device, comprising the steps of:
receiving an endocardial acceleration (EA) signal from a sensor coupled to the implantable medical device;
extracting from the EA signal a predetermined EA parameter, and storing the EA parameter for successive cardiac cycles during a first predetermined period;
calculating a variability in the EA parameter during the first predetermined period;
comparing the calculated variability in the EA parameter to a reference variability value of said EA parameter to determine a variability ratio, wherein the reference variability value is a calculated variability of a second predetermined period of the patient, wherein the second predetermined period occurs before the first predetermined period; and
determining whether the variability ratio crosses a predetermined threshold, wherein crossing of the predetermined threshold indicates a deterioration in the patient heart function.

19. The method of claim 18, wherein the EA parameter is the peak-to-peak amplitude of a first peak in the EA parameter, and wherein the variability in the EA parameter is indicative of an increase in sleep apneas experience by the patient.

20. The method of claim 18, further comprising providing an alert indicative of crossing the predetermined threshold and a deterioration in the patient heart function.

* * * * *